United States Patent
Ranganathan et al.

(10) Patent No.: US 7,160,535 B2
(45) Date of Patent: Jan. 9, 2007

(54) CONJUGATES OF ANTIOXIDANTS WITH METAL CHELATING LIGANDS FOR USE IN DIAGNOSTIC AND THERAPEUTIC APPLICATIONS

(75) Inventors: Ramachandran S. Ranganathan, Princeton, NJ (US); Helen Fan, Plainsboro, NJ (US); Michael F. Tweedle, Princeton, NJ (US)

(73) Assignee: Bracco International BV, Amsterdam (NL)

( * ) Notice: Subject to any disclaimer, the term of this patent is extended or adjusted under 35 U.S.C. 154(b) by 598 days.

(21) Appl. No.: 10/399,265

(22) PCT Filed: Oct. 31, 2001

(86) PCT No.: PCT/US01/46002

§ 371 (c)(1),
(2), (4) Date: Aug. 15, 2003

(87) PCT Pub. No.: WO02/40060

PCT Pub. Date: May 23, 2002

(65) Prior Publication Data

US 2004/0082767 A1 Apr. 29, 2004

(51) Int. Cl.
*A61K 51/00* (2006.01)

(52) U.S. Cl. .................. 424/1.65; 424/9.1; 424/9.3
(58) Field of Classification Search .... 424/9.36–9.365, 424/1.65, 9.1; 540/464–474
See application file for complete search history.

(56) References Cited

OTHER PUBLICATIONS

Beaupere, D. et al; "Selective Azidation of L Sorbose Application to the Rapid Synthesis of 1 Deoxynojirmycin", *Carbohydrate Research*, vol. 191, No. 1, pp. 163-166, 1989.
Lewis, M et al.; "Maleimidocysteineamido-DOTA derivatives: New Reagents for Radiometal Chelate Conjugation to Antibody Sulfhydryl Groups", *Bioconjugate Chemisty*, vol. 9, No. 1, Jan. 1998.
Ranganathan, R. et al.; "Synthesis of Conjugates of Ascorbic Acid with Metal Chelates", *Abstracts of Papers American Chemical Society*, vol. 221, No. 1-2, p. Carb 59, 2001.
PCT Search Report for PCT/US01/46002 mailed Jun. 11, 2003.

*Primary Examiner*—Michael G. Hartley
*Assistant Examiner*—Melissa Perreira
(74) *Attorney, Agent, or Firm*—Kramer Levin Naftalis & Frankel LLP

(57) ABSTRACT

The invention provides radiopharmaceuticals for diagnostic and therapeutic applications, conjugates of antioxidants with metal chelating ligands, intermediate compounds, methods of making such radiopharmaceuticals, ligands, and intermediate compounds, and kits for preparing the radiopharmaceutical complexes.

7 Claims, No Drawings

CONJUGATES OF ANTIOXIDANTS WITH METAL CHELATING LIGANDS FOR USE IN DIAGNOSTIC AND THERAPEUTIC APPLICATIONS

FIELD OF INVENTION

The present invention relates to diagnostic and therapeutic compositions, methods of their use, and processes of their preparation.

BACKGROUND OF INVENTION

Ascorbic acid (vitamin C) and other antioxidants, such as α-tocopherol, minimize tissue damage caused by oxidative metabolic processes and also have acceptable biological tolerance. Recently, an ascorbic acid derivative with antioxidant properties, 2-O-octadecylascorbic acid, has been prepared and has been shown to markedly inhibit the myocardial lesions induced by ischemia-reperfusion treatment in rats. Ascorbic acid may also bind to the human serum albumin (HSA) weakly with a binding constant of about $3.5 \times 10^4$ $M^{-1}$. Ascorbic acid and other antioxidants have been used to stabilize radiopharmaceuticals by decreasing the oxidation of substituents due to radical reactions induced by the decay of the radionuclide.

Metal chelating ligands-are designed for use in Nuclear Medicine, Magnetic Resonance Imaging (MRI), and neutron capture therapy applications. Magnetic resonance (hereinafter sometimes referred to as MR) imaging is widely used for obtaining spatial images of parts of a patient for clinical diagnosis. Typically, the image is obtained by placing the patient in a strong external magnetic field and observing the effect of this field on the magnetic properties of protons contained in and surrounding the organ or tissue of the patient. The proton relaxation times, called $T_1$ or spin-lattice or longitudinal relaxation time, and $T_2$ or spin-spin or transverse relaxation time depend on the chemical and physical environment of the organ or tissue being imaged. In order to improve the clarity of the image, a diagnostic agent is administered intravenously (hereinafter sometimes referred to as I.V.) and is taken up by the organs, such as the liver, spleen, and lymph nodes to enhance the contrast between healthy and diseased tissues.

The contrast agents used in MR imaging derive their signal-enhancing effect from the inclusion of a material exhibiting paramagnetic, ferrimagnetic, ferromagnetic or superparamagnetic behavior. These materials affect the characteristic relaxation times of the imaging nuclei in the body regions into which they distribute causing an increase or decrease in MR signal intensity. There is a need for contrast agents such as those of the present invention, that selectively enhance signal intensity in particular tissue types, as most MR contrast agents are relatively non-specific in their distribution.

Nuclear medicine procedures and treatments are based on internally distributed radioactive materials, such as radiopharmaceuticals or radionuclides, which emit electromagnetic radiations as alpha or beta particles or as gamma rays or photons. Following I.V., oral or inhalation administration, gamma rays are readily detected and quantified within the body using instrumentation such as scintillation and gamma cameras. Compounds derivatized with alpha or beta emitters may be used for radiotherapeutic applications, providing an internal dose of cytotoxic radiation at their target tissues(s).

SUMMARY OF THE INVENTION

The invention relates to conjugates of an antioxidant and one or more metal chelating ligands that may be chelated to radioactive or non-radioactive metals and use of such conjugates chelated to such metals as, for example:
  a) Magnetic resonance diagnostic compositions for visualization of tissues and compartments that bind or utilize an antioxidant conjugated to metal chelates;
  b) Radiodiagnostic compositions for visualization of tissues, comprising ligands chelated to radioactive gamma-emitting metals and coupled to said antioxidant conjugates; and
  c) Compositions for radiotherapy or for neutron capture therapy, comprising ligands chelated to radioactive alpha or beta-emitting metals or to metals suitable for neutron capture therapy and coupled to said antioxidant conjugates.

In one embodiment, the invention provides novel conjugates of antioxidants and metal chelating ligands. The invention also provides novel intermediates, methods of making the conjugates and intermediates, methods of stabilizing radiopharmaceutical ligands, and kits for preparing radiopharmaceuticals. Antioxidants which may be used in the present invention include ascorbic acid, para-aminobenzoic acid (PABA), cysteine, monothioglycerol, and gentisic acid. Ascorbic acid is a preferred antioxidant of the invention.

In a preferred embodiment, the invention provides a compound having the following chemical structure:

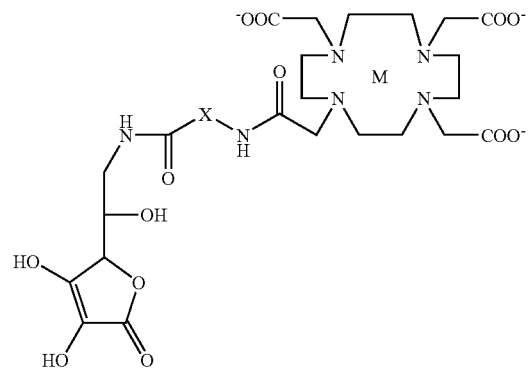

wherein M is $^{99m}$Tc, $^{51}$Cr, $^{67}$Ga, $^{68}$Ga, $^{111}$In, $^{168}$Yb, $^{140}$La, $^{90}$Y, $^{88}$Y, $^{86}$Y, $^{153}$Sm, $^{166}$Ho, $^{165}$Dy, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{215}$Bi, $^{177}$Lu, chromium (III),manganese (II), iron (II), iron (III), cobalt (II), nickel (II), copper (II), praseodymium (III),neodymium (III), samarium (III), gadolinium (III), terbium, (III), dysprosium (III), holmium (III), erbium (III) or ytterbium (III); and X is $CH_2$, an amino acid, a peptide, a protein, or an antibody.

In one preferred embodiment, X is $CH_2$. In another preferred embodiment, X is the amino acid represented by the chemical structure:

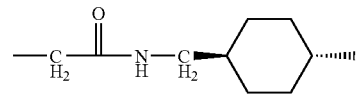

In certain preferred embodiments, the metal (M) is $^{99m}$Tc, $^{186}$Re, $^{188}$Re, $^{90}$Y, $^{88}$Y, $^{86}$Y, $^{177}$Lu, or gadolinium (III).

In another embodiment, the invention provides kits for preparing a radiopharmaceutical. Kits of the invention include an oxidant covalently bound to a complexing (or radiopharmaceutical ligand). In preferred embodiments, the kit includes a targeting molecule bound to the antioxidant, the ligand, or, most preferably, both. In certain of these embodiments, the targeting molecule is an amino acid, a peptide, a protein, or an antibody.

In yet another embodiment, the invention provides methods of stabilizing a radiopharmaceutical ligand, which optionally includes a targeting molecule, by conjugating the radiopharmaceutical ligand with an antioxidant.

DETAILED DESCRIPTION OF THE INVENTION

The following abbreviations are used in this specification: "DOTA" means 1,4,7,10-tetraazacyclododecane-1,4,7,10-tetraacetic acid; "HATU" means O-(7-azabenzotriazol-1-yl)-1,1,3,3-tetramethyluronium hexafluorophosphate; "DIEA" means diisopropylethylamine; "DMF" means N,N-dimethylformamide; "TsCl" means p-toluenesulfonyl chloride; "THF" means tetrahydrofuran; "TFA" means trifluoroacetic acid; and "RT" means room temperature. In addition, the terms "chelating ligand," "complexing ligand," and "radiopharmaceutical ligand" are used interchangeably throughout this specification, except where the context requires otherwise.

The present invention is directed, in part, to conjugates of an antioxidant, such as ascorbic acid, and one or more polydentate macrocyclic or non-macrocyclic metal-chelating ligand residues that are optionally chelated to radioactive or non-radioactive metals capable of either being detected by imaging means for diagnosis or capable of providing a therapeutic or radiotherapeutic effect. The metal chelating groups can be either macrocyclic or non-macrocyclic multidentate metal chelating ligands, and the structure of these ligands and the metals that are chelated to them may be varied depending on the use envisioned for them. For example, for compounds of the present application that are used for Magnetic Resonance Imaging applications, chelating polyaza macrocyclic ligands that form stable compounds with superparamagnetic or paramagnetic metals, and chelating ligands that provide enhanced relaxivity properties (vide infra) are preferred. For such applications, gadolinium is the preferred metal.

In a further embodiment, conjugates of the present invention may be used for radiodiagnostic or radiotherapeutic purposes. In this application, an antioxidant, such as ascorbic acid, is conjugated to a chelating ligand, which form stable complexes with radioactive metals. The chelating ligands that may be used in the practice of the present invention are not particularly limited and are well known to those skilled in the art. Such ligands include, for example, Oxa-PnAO ligands and peptide analogue chelators, such as those with an N$_3$S configuration. Radioactive metals include the elements having atomic numbers of 22 to 29, 42, 44 and 58–70. For example, radioactive isotopes include: $^{99m}$Tc, $^{51}$Cr, $^{67}$Ga, $^{68}$Ga, $^{111}$In, $^{168}$Yb, $^{140}$La, $^{90}$Y, $^{88}$Y, $^{86}$Y, $^{153}$Sm, $^{166}$Ho, $^{165}$Dy, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{215}$Bi, and $^{177}$Lu. The choice of metal ion will be determined based on the desired therapeutic or diagnostic application. Where $^{99m}$Tc is the radioactive metal used, Oxa-PnAO ligands or N,N-Me$_2$-Gly-Ser-Cys-Gly are preferably used to form conjugates with an antioxidant, such as ascorbic acid.

The antioxidants used in the invention are not particularly limited, provided that the antioxidant can be conjugated to a ligand and/or targeting molecule, as described herein. For example, antioxidants which may be used in the present invention include ascorbic acid, para-aminobenzoic acid (PABA), cysteine, monothioglycerol, and gentisic acid. Of these, ascorbic acid is preferred.

The conjugates may further comprise targeting molecules such as, for example, proteins, peptides and antibodies that localize to desired areas of the body. Preferred targeting molecules are peptides or analogues thereof and may include a monomer or multimer of one or more peptides. Examples of suitable targeting molecules include gastrin releasing peptide (GRP) agonists, such as those disclosed in U.S. Pat. No. 6,200,546, incorporated herein by reference in its entirety. Other useful targeting molecules include those disclosed in U.S. Pat. Nos. 5,662,885; 5,780,006; and 5,976,495, incorporated herein by reference in their entirety, and particularly monomers or multimers of TKPPR or analogues thereof. Analogues of a peptide include molecules that target the peptide's receptor with the same or greater avidity, as well as muteins, retropeptides and retroinversion peptides. One of ordinary skill will appreciate that these analogues may also contain modifications such as substitutions, deletions and/or additions of one or several amino acids, insofar as these modifications do not alter the biological activity of the peptide in a significantly negative manner.

General structures of Oxa-PnAO ligands are detailed in U.S. Pat. No. 6,093,382, which is incorporated by reference herein. These conjugates are intended for preparation of compounds for use in nuclear medicine and radiotherapy applications and are based on the general oxa-PnAO ligand class described in U.S. Pat. No. 5,608,110, which are incorporated by reference herein. For diagnostic applications, $^{99m}$Tc is the preferred metal.

Structures and preparation of peptide-derived N$_3$S radionuclide chelators are discussed in U.S. Pat. Nos. 5,662,885; 5,780,006 and 5,976,495, each of which is incorporated herein by reference in its entirety. Particularly preferred N$_3$S chelators are N,N-dimethyl-Gly-Ser-Cys-Gly and N,N-dimethyl-Gly-t-butylGly-Cys-Gly.

Radiopharmaceutical conjugates (either diagnostic or therapeutic) of the present invention confer the added benefit of introducing an antioxidant (such as ascorbic acid) in close proximity to the oxidizable groups on the radiopharmaceutical (either diagnostic or therapeutic). Such oxidizable groups may include, for example, peptides containing methionine or free thiols. Further, such oxidizable groups may be located on either the ligand or a targeting molecule. This covalent attachment of an antioxidant and the chelator (optionally coupled to a targeting ligand) provides additional stability due to the close proximity of the antioxidant to substituents on the radiopharmaceutical that are susceptible to oxidation induced by the decay of the radionuclide. Indeed, it has been reported that the ester of 6-hydroxy ascorbic acid retains a number of useful antioxidant properties. The amide bond introduced into 6-hydroxy ascorbic acid in the compounds disclosed herein is expected to have greater serum stability than the ester compounds previously disclosed, and thus, to exhibit antioxidant behavior. Therefore, the ascorbic acid or other antioxidant derivatives of the invention are expected to retain their antioxidant properties when conjugated to the chelator and/or targeting molecules, thereby improving the stability of the conjugates.

Specifically, where a targeting ligand is used, the antioxidant may be attached to the targeting molecule, which is attached to the chelating ligand. For example, where ascorbic acid is the antioxidant used, 6-amino ascorbic acid may be attached to the C-terminus of a peptide targeting molecule or via the beta or gamma carboxyl group of an aspartic or glutamic acid in the peptide. Similarly, the 6-amino ascorbic acid could be attached to the N-terminus of the peptide via a di-carboxylic acid such as succinic acid.

Alternatively, in the absence of a targeting molecule, the antioxidant may be attached to the chelating ligand as shown herein, or using methods known to those skilled in the art.

Examples of paramagnetic metals include the elements having atomic numbers of 22 to 29, 42, 44 and 58–70. Examples of such metals are chromium (III), manganese (II), iron (II), iron (III), cobalt (II), nickel (II), copper (II), praseodymium (III), neodymiu (III), samarium (III), gadolinium (III), terbium, (III), dysprosium (III), holmium (III), erbium (III) and ytterbium (III). Chromium (III), manganese (II), iron (III) and gadolinium (III) are preferred.

In one embodiment of the invention, two conjugates of ascorbic acid with DOTA were prepared, conjugates 22a and 22b. These conjugates have the following structure:

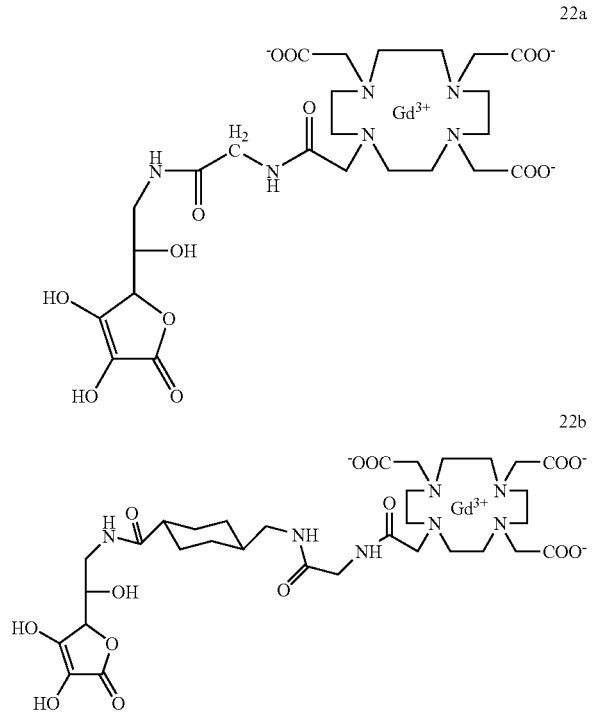

These two conjugates were synthesized as described below.

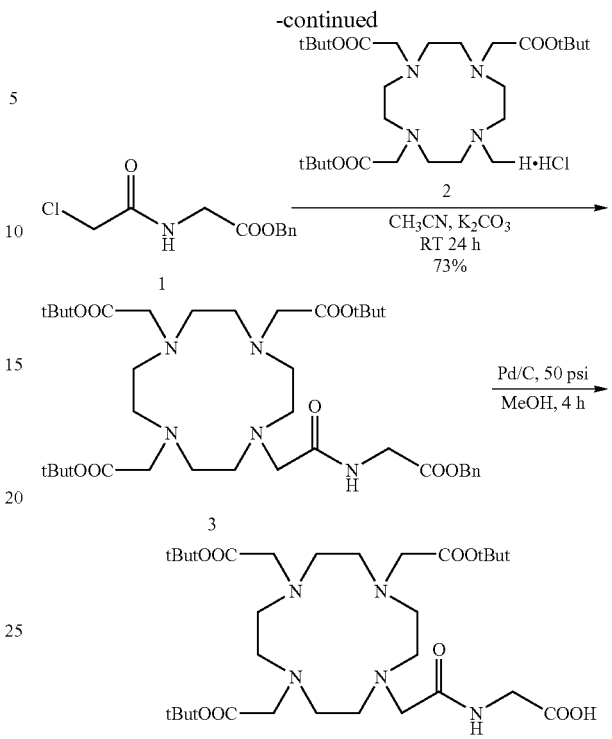

DOTA-G-tri-t-butyl ester 4, an intermediate compound in the synthesis of the conjugate 22, was synthesized starting with glycine benzylester hydrochloride (Aldrich), as described in Scheme 1. Chloroacetylchloride (Aldrich) was added to glycine benzylester hydrochloride in the presence of $K_2CO_3$ to produce N-(chloroacetyl)-glycine benzyl ester 1. The ester 1 was added to a suspension of DO3A-tri-t-butyl ester hydrochloride 2 (see U.S. Pat. No. 5,573,752) in $K_2CO_3$ to produce DOTA-G-tri-t-butyl-benzyl ester 3. Subsequent catalytic hydrogenation produced the DOTA-G-tri-t-butyl ester 4.

Methyl 6-amino-6-deoxy-2,3-O-isopropylidene-2-keto-L-gulonate 16, which was a key protected intermediate for the synthesis of the conjugate 22, was synthesized starting from (2S,8S,1R,6R)-4,4,11,11-tetramethyl-3,5,7,10,12-pentaoxatricyclo[6.4.0.0<2,6>]dodecane-6-carboxylic acid 9. The compound was synthesized as described in Scheme 2. The commercially available acid 9 was methylated by MeI in the presence of $K_2CO_3$. Mono-deprotection of the methyl ester 10 by $Cu(OAc)_2$ in $H_2O$ produced the diol 11. The sulfite 12 was prepared from the diol 11 using thionyl chloride in the presence of $Et_3N$. Oxidation of the sulfite 12 with $NaIO_4/RuCl_3$ gave the cyclic sulfate 13. Treatment of the sulfate 13 with $NaN_3$ in $CH_3CN$ (acetonitrile), in the presence of $Me_4N^+Cl^-$ as a phase transfer catalyst, effected the ring opening with $N_3^-$ substitution to provide the azide 14. Subsequent hydrolysis and catalytic hydrogenation of the azide 14 produced the desired amine 16 in an overall yield of 6.9%.

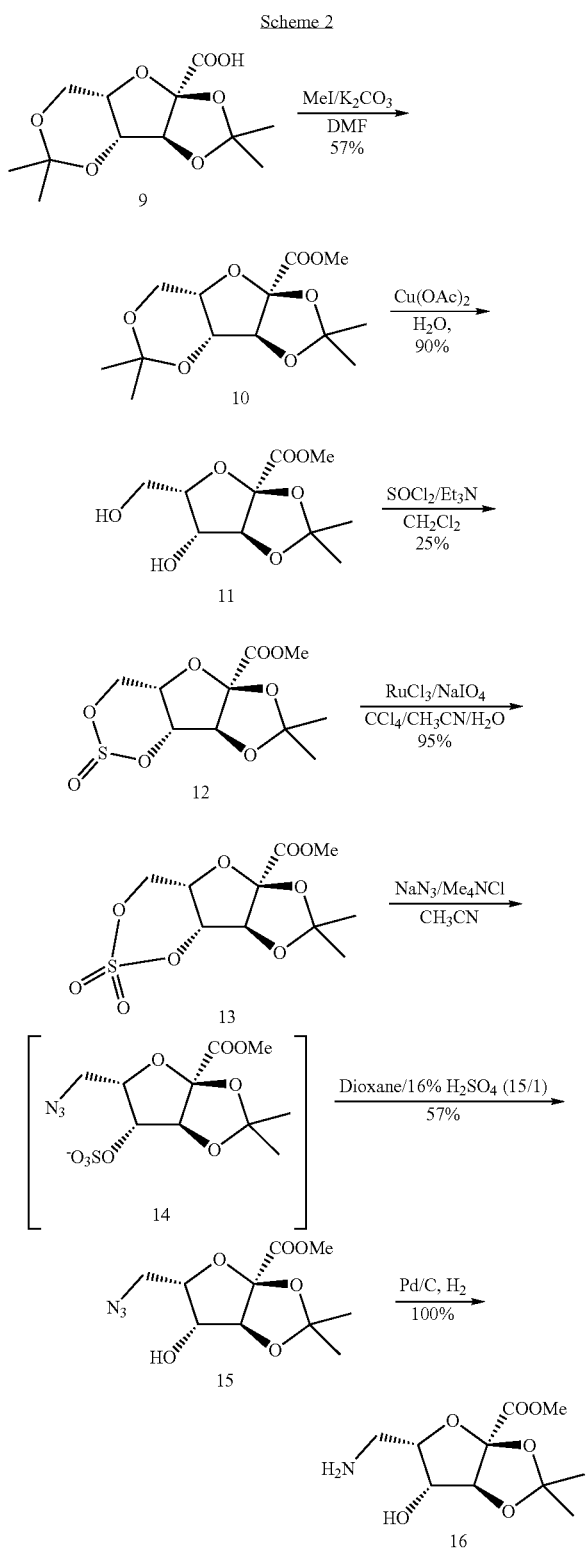

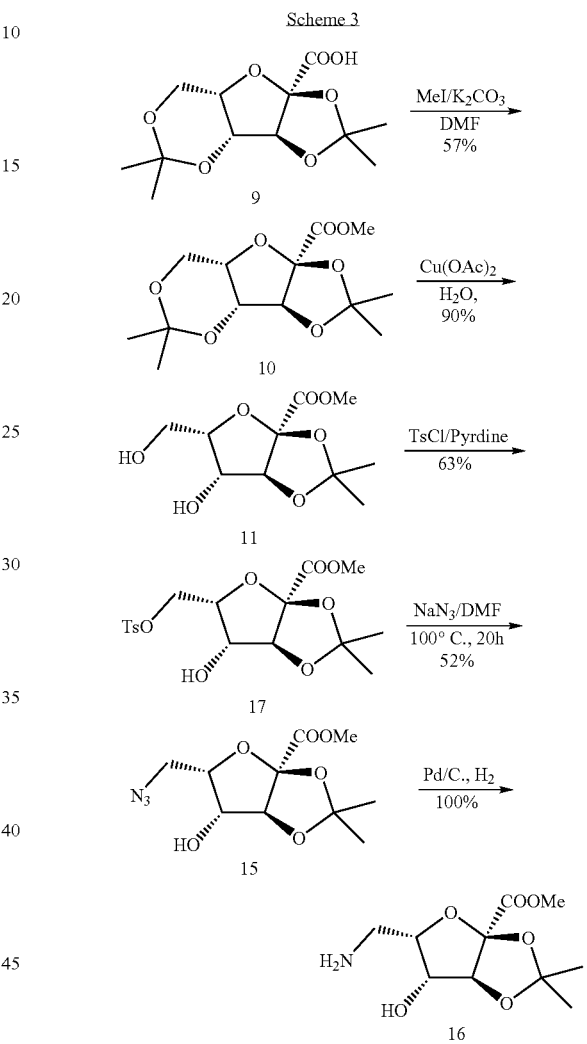

pyridine in 63% yield. Tosylate 17 was treated with NaN₃ in DMF at 100° C. for 16 hours that produced the substituted azide 15 as a clean product by TLC. The pure material 15 was isolated by silica column chromatography providing a 52% yield. Subsequent catalytic hydrogenation produced the desired amine 16 in an overall yield of 16.8%

In an alternative embodiment for synthesizing compound 16, displacement of the —OTs group by $N_3^-$ in 6-O-p-toluenesulfonyl-4-hydroxy-gulonate 17 was achieved and is illustrated in Scheme 3. The mono-tosylate 17 was prepared by treatment of the diol 11 with one equivalent of TsCl in The method of synthesis of the ascorbic conjugates from methyl (5S,7S, 1R,6R)-7-(aminomethyl)-6-hydroxy-3,3-dimethyl-2,4,8-trioxabicyclo[3.3.0]octanecarboxlate 16 is shown in Scheme 4. To obtain the desired conjugate 22a, the amine 16 was first coupled with DOTA-G-tri-t-butyl ester 4 (synthesized as in Scheme 1) in the presence of HATU/Et₃N to obtain compound 19a. Basic hydrolysis of compound 19a produced the tris-t-Bu-DOTA-G-CH₂-gulonic acid conjugate 20a. Further deprotection of compound 20a was investigated under several conditions as follows: 1) 6N HCl/THF 1/1, v/v, 45° C. for 7 h; 2) 4.5N H₂SO₄/THF (1/1, v/v), RT for 16 h; 3) TFA/H₂O (7/1, v/v), RT for 16 h. Of these methods, method 1 gave the highest yield of 30% for the conjugate 21a, after purification by HPLC. Chelation with gadolinium produced the ascorbic-Gd chelate conjugate 22a in an overall yield of 13% from compound 16.

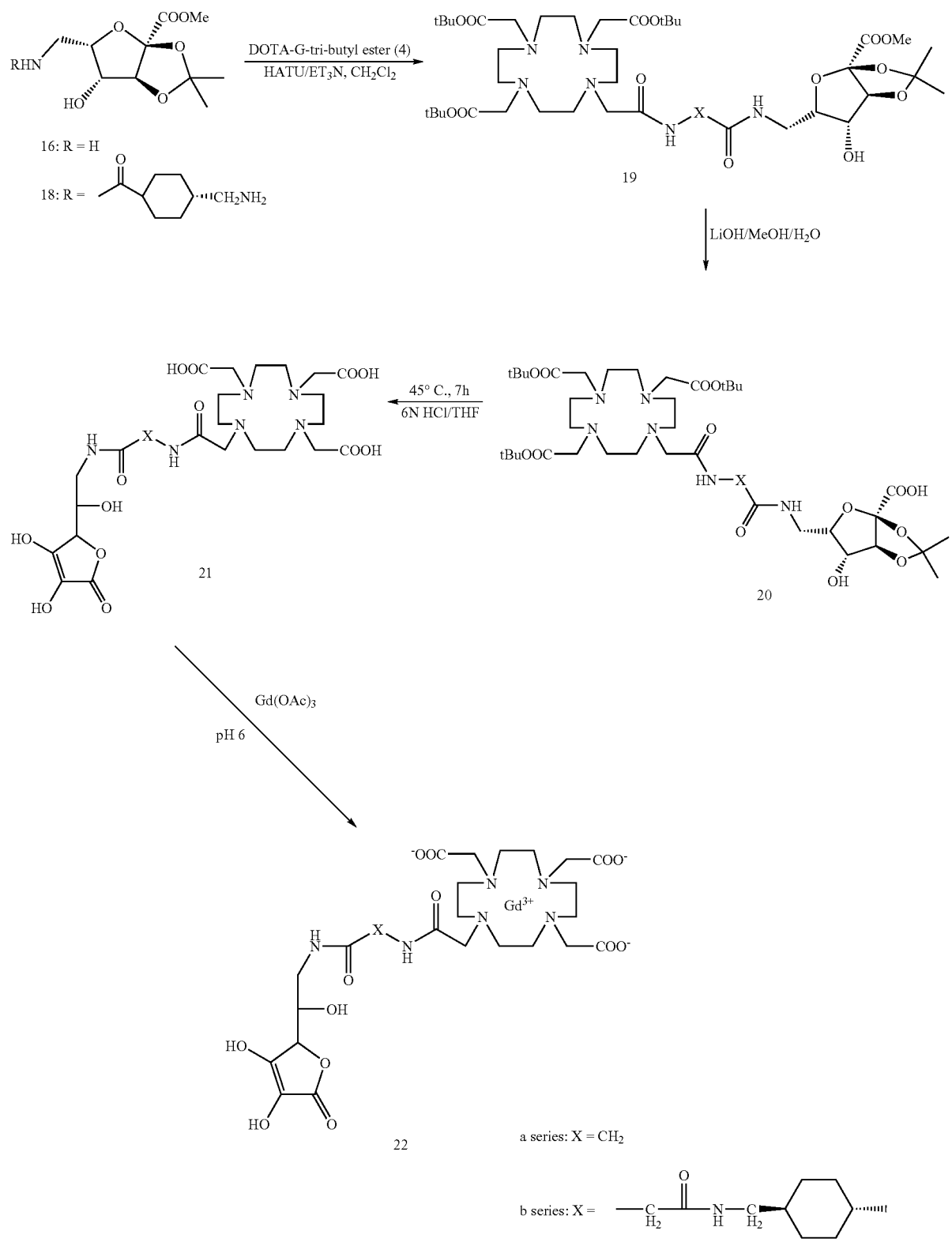

Following a similar approach, but by starting from 6-[trans-4-(aminomethyl)-cyclohexyl-1-carbonyl]-amino-6-deoxy-2,3-isopropylidene-2-keto-gulonate 18, the ascorbic-Gd chelate conjugate 22b was obtained, containing a longer linker residue in an overall yield of 4.8%. The final products and intermediates were characterized by mass spectra, elemental analysis, and NMR, as detailed in the Example section below. The 6-[trans-4-(aminomethyl)-cyclohexyl-1-carbonyl]-amino-6-deoxy-2,3-isopropylidene-2-keto-gulonate 18 was synthesized as shown in Scheme 5.

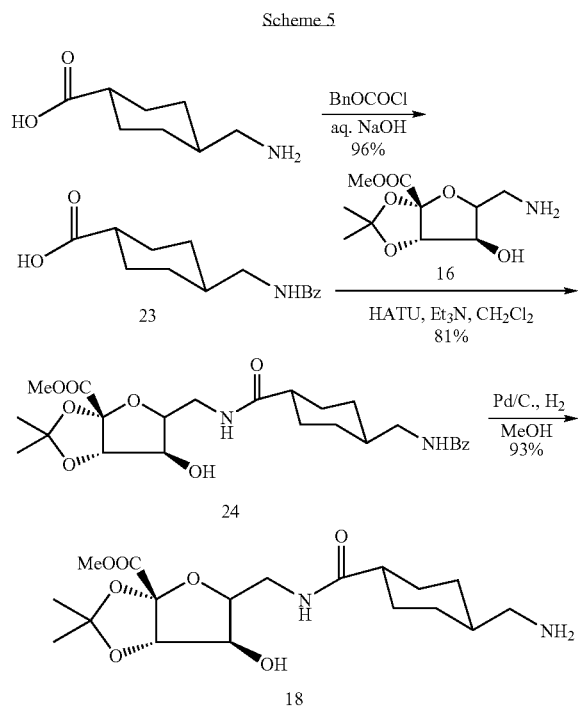

Scheme 5

Relaxivity of a paramagnetic material in the presence of a large protein such as human serum albumin may be used to study the ability of the compounds of the present invention to bind the target protein. As such, when a small molecule binds a large protein, the relaxivity of the former will increase because of an increase in its rotational correlation time. This increase in relaxivity may be used not only to measure the extent of binding but also to evaluate the viability of the paramagnetic agent as a blood pool contrast medium.

The relaxivity of the conjugates 22a and 22b in water as well as in water containing a known amount (20%, v/v) of a HSA preparation, known as, seronom (Table 1) were studied.

The relaxation time of the samples (22a or 22b) in seronom ($T1_{Gd\text{-}ligand\ in\ seronom}$) and in water ($T1_{Gd\text{-}ligand\ in\ water}$) were measured at 38° C. using an IBM PC/20 multispec relaxometer. The relaxivity of the samples in seronom ($r1_{Gd\text{-}ligand\ in\ seronom}$) and in water ($r1_{Gd\text{-}ligand\ in\ water}$) were calculated by the following equations:

$$r1_{Gd\text{-}ligand\ in\ seronom} = (1/T1_{Gd\text{-}ligand\ in\ seronom} - 1/T1_{seronom})/[Gd\text{-}ligand]$$

$$r1_{Gd\text{-}ligand\ in\ water} = (1/T1_{Gd\text{-}ligand\ in\ water} - 1/T1_{water})/[Gd\text{-}ligand],$$

where [Gd-ligand] is the concentration of the chelate 22a or 22b, which was determined by ICP[11]; $T1_{seronom}$ is the relaxation time for pure aqueous seronom; $T1_{water}$ is the relaxation time for pure water.

After the measurement, the sample in aqueous seronom was placed in a centrifree micropartition device (Millipore, Beverly, Mass.). The device was centrifuged at 500×g for 45 mm in a fixed angle rotor (Beckman Model J2-21M, JA-20 rotor). The solution (0.5 mL) was taken from below the filter (unbound Gd-ligand) for [Gd] ICP measurement. The [Gd] of the uncentrifuged sample was also measured as a control. The Fraction Bound was calculated by the following equation:

Fraction Bound=([Gd-ligand]$_{control}$−[Gd-ligand]$_{unbound}$)/[Gd-ligand]$_{control}$. Table 1 details the results of the tests.

TABLE 1

| Compound | Relaxivity in water (mM$^{-1}$s$^{-1}$) $r1_{Gd\text{-}ligand\ in\ water}$ | Relaxivity in aqueous seronom (mM$^{-1}$s$^{-1}$) $r1_{Gd\text{-}ligand\ in\ seronom}$ | Fraction bound |
|---|---|---|---|
| 22a | 4.83 | 6.38 | 8.8% |
| 22b | 7.20 | 8.18 | 10.9% |

Table 1 shows that the increase in relaxivity in the presence of seronom is 32% and 14% in the case of 22a and 22b, respectively. Based on these results, it is believed that the binding of these conjugates with HSA may not be strong enough for commercial blood pool MRI applications. However, the described conjugates 22a and 22b may be useful as extravascular MRI contrast agents. Moreover, the chemistry described and the conjugates made herein may be used in other applications such as those discussed herein and may be particularly useful where antioxidant properties of ascorbic acid may be required.

It is understood that, for radiopharmaceutical or radiotherapy applications, it is convenient to prepare the complexes of the present invention at, or near, the site where they are to be used. A single, or multi-vial kit that contains all of the components needed to prepare the complexes of this invention, other than the radionuclide ion itself, is an integral part of this invention. The amount administered may be selected based on the desired use, such as to produce a diagnostic image of an organ or other site of a subject or a desired radiotherapeutic effect, by methods known in the art. Exemplary dosages are those employing about 2–200 mCi rhenium, lutetium, or yttrium (for radiotherapy), or about 10–60 mCi technetium (for imaging).

Kits of the present invention comprise one or more vials containing the sterile formulation of a predetermined amount of a complexing ligand, an oxidant and optionally other components such as reducing agents, transfer ligands, buffers, lyophilization aids or bulking agents, stabilization aids, solubilization aids and bacteriostats. The inclusion of one or more optional components in the formulation will frequently improve the ease of synthesis of the radiopharmaceutical by the practicing end user, the ease of manufacturing the kit, the shelf-life of the kit, or the stability and shelf-life of the radiopharmaceutical. The improvement achieved by the inclusion of an optional component in the formulation must be weighed against the added complexity of the formulation and added cost to manufacture the kit. The one or more vials that contain all or part of the formulation can independently be in the form of a sterile solution or a lyophilized solid.

Buffers useful in the preparation of radiopharmaceuticals and in diagnostic kits useful for the preparation of the radiopharmaceuticals include but are not limited to phosphate, citrate, sulfosalicylate, and acetate. A more complete list can be found in the United States Pharmacopeia.

Lyophilization aids or bulking agents useful in the preparation of diagnostic kits useful for the preparation of radiopharmaceuticals are known in the art and include lactose, sodium chloride, maltose, sucrose, PEG 8000, cyclodextrins, such as hydroxypropyl-γ-cyclodextrin (BP-γ-CD), dextran, Ficoll and polyvinylpyrrolidine (PVP).

Stabilization aids, such as antioxidants, useful in the preparation of radiopharmaceuticals and in diagnostic kits for the preparation of radiopharmaceuticals include but are not limited to ascorbic acid, para-aminobenzoic acid (PABA), cysteine, monothioglycerol, sodium bisulfite, sodium metabisulfite, gentisic acid, and inositol. One skilled in the art will appreciate that while conjugates of ascorbic acid are exemplified, the invention includes conjugates of other antioxidants. Also, in addition to the covalent attachment of an antioxidant to a complexing ligand discussed herein, one or more additional stabilzation aids may be added to formulations of the conjugates of the invention.

Solubilization aids useful in the preparation of radiopharmaceuticals and in diagnostic kits useful for the preparation of the radiopharmaceuticals include but are not limited to ethanol, glycerin, polyethylene glycol, propylene glycol, polyoxyethylene sorbitan monooleate, sorbitan monooloeate, polysorbates, poly(oxyethylene)poly(oxypropylene)poly(oxyethylene) block copolymers (Pluronics) and lecithin. Preferred solubilizing aids are polyethylene glycol, and Pluronics.

Bacteriostats useful in the preparation of radiopharmaceuticals and in diagnostic kits useful for the preparation of the radiopharmaceuticals include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or co-ligand and so forth.

The predetermined amounts of each component in the formulation are determined by a variety of considerations familiar to those skilled in the art. These considerations are in some cases specific for that component and in other cases dependent on the amount of another component or the presence and amount of an optional component. In general, the minimal amount of each component is used that will give the desired effect of the formulation. The desired effect of the formulation is that the practicing end user can synthesize the radiopharmaceutical and have a high degree of certainty that the radiopharmaceutical can be safely injected into a patient and will provide diagnostic information about the disease state of that patient.

The present invention will be illustrated in greater detail by the following specific examples. It is understood that these examples are given by way of illustration and are not meant to limit the disclosure or claims. Moreover, these examples are meant to further demonstrate that the synthesis of conjugates of ascorbic acid with macrocyclic polyaminopolycarboxylates chelates. All percentages in the examples or elsewhere in the specification are by weight unless otherwise specified.

EXAMPLE 1

The synthesis of methyl (3aS,3bR,7aS,8aR)-2,2,5,5-tetramethyltetrahydro-8aH-[1,3]dioxolo[4,5]furo[3,2-d][1,3]dioxine-8a-carboxylate 10 is detailed.

To a solution of (3aS,3bR,7aS,8aR)-2,2,5,5-tetramethyltetrahydro-8aH-[1,3]dioxolo[4,5]furo[3,2-d][1,3]dioxine-8a-carboxylic acid monohydrate 9 (10 g, 34.2 mmol, Aldrich) in DMF (anhydrous, 32 mL, Aldrich) was mixed with $K_2CO_3$ (3.4 g, 24.8 mmol, Aldrich). MeI (7.1 g, 50 mmol, Aldrich) was added dropwise through a dropping funnel. The resulting mixture was stirred at room temperature for 16 h. The solvent was removed in vacuo and the residue was dissolved in EtOAc (100 mL). It was washed with $H_2O$ (2×60 mL), brine (1×50 mL) and dried over $MgSO_4$. EtOAc was evaporated. The crude material was purified by silica gel chromatography using EtOAc/Hexane to obtain product 10 (5.6 g; yield 57%).

TLC: Silica gel, $R_f$ 0.45, EtOAc/hexane 1/4.

$^1$HNMR ($CDCl_3$, ppm): 1.35, 1.40, 1.50 (s, 12H, $CH_3$'s on the two isopropylidine rings); 3.85 (s, 3H, $OCH_3$); 4.08, (m, 2H, $CH_2$); 4.15, 4.30, 4.85 (s, 3H, CH's on C-3, C-4, C-5). Mass spectrum: 311.3 $(M+Na)^+$; 289.3 $(M+H)^+$.

EXAMPLE 2

The synthesis of Methyl (3aS,5R,6S,6aR)-6-hydroxy-5-(hydroxymethyl)-2,2-dimethyldihydrofuro[2,3-d][1,3]dioxole-3a(5H)-carboxylate 11 is detailed.

To a suspension of compound 10 (5.6 g, 18.3 mmol) in $H_2O$ (65 mL) was added a solution of $Cu(OAc)_2.H_2O$ (25 mg, Aldrich) in $H_2O$ (5 mL). It was refluxed (oil bath) for 15 min. The solution became clear. This solution was cooled and evaporated to dryness. Purification of the residue by silica gel chromatography using EtOAc/Hexane afforded product 11 as a waxy solid (4.1 g; yield 90.3%).

TLC: Silica gel, $R_f$ 0.70, EtOAc.

$^1$HNMR ($CDCl_3$, ppm): 1.40, 1.50 (s, 6H, $CH_3$'s on the isopropylidine ring); 3.85 (s, 3H, $OCH_3$); 3.98–4.00 (m, 1H, CH on C-4); 4.10–4.13 (m, 1H, CH on C-5); 4.80 (s, 2H, $CH_2$); 4.75 (m, 1H, CH on C-3). Mass spectrum: 271.2 $(M+Na)^+$; 249.3 $(M+H)^+$.

EXAMPLE 3

Two different synthesis processes of Methyl (3aR,5S,6R)-5-(azidomethyl)-6-hydroxy-2,2-dimethyldihydrofuro[2,3-d][1,3]dioxole-3a(5H)-carboxylate 15 are detailed.

Example 3A

From Sulfite 12 and Sulfate 13 (Scheme 2)

i) Methyl (4aS,5aR,8aS,8bR)-7,7-dimethyltetrahydro-5aH-[1,3]dioxolo[4,5]furo[3,2-d][1,3,2]dioxathiine-5a-carboxylate 2-oxide 12

To a solution of the diol 11 (3.4 g, 13.7 mmol) and triethylamine (0.58 mol, 80 mL) in $CH_2Cl_2$ (40 mL) was added dropwise a solution of $SOCl_2$ (2.3 g, 19.2 mmol, Aldrich) in $CH_2Cl_2$ (2 mL) at 0° C. It was stirred at 0° C. for 15 min. It was then diluted with cold ether (80 mL), washed with cold water (150 mL×2), dried over $MgSO_4$ and evaporated in vacuo. Purification by silica column chromatography afforded product 12 (1 g, yield 25%).

TLC: Silica gel, R$_f$ 0.70, EtOAc/hexane 1/1.

$^1$HNMR (CDCl$_3$, ppm): 1.40, 1.50 (s, 6H, CH$_3$'s on the isopropylidine ring); 3.90 (s, 3H, OCH$_3$); 4.2 (d, 1H, CH on C-3); 4.31 (m, 1H, CH on C5); 4.92 (m, 1H, CH on C-4); 4.98 (m, 2H, CH on C-6). Mass spectrum: 317.1 (M+Na)$^+$.

ii) Methyl (4aS,5aR,8aS,8bR)-7,7-dimethyltetrahydro-5aH-[1,3]dioxolo[4,5]furo[3,2-d][1,3,2]dioxathiine-5a-carboxylate 2,2-dioxide 13

To a solution of the sulfite 12 (1 g, 3.4 mmol) in CCl$_4$/CH$_3$CN (10 mL, 1/1 v/v) was added a suspension of RuCl$_3$.xH$_2$O (1 mg) and NaIO$_4$ (2.9 g, 13.6 mmol) in H$_2$O (10 mL) at 0° C. The mixture was stirred vigorously at RT for 7 h. It was diluted with ether (20 mL), washed with water (30 mL×2), sat. NaHCO$_3$ (30 mL×1), and dried over MgSO$_4$. Evaporation of the solution afforded product 13 as a white crystalline solid (1 g, yield 95%). The material was directly used without purification.

TLC: Silica gel, R$_f$ 0.60, EtOAc/hexane 1/1.

$^1$HNMR (CDCl$_3$, ppm): 1.41, 1.51 (s, 6H, CH$_3$'s on the isopropylidine ring); 3.88 (s, 3H, OCH$_3$); 4.38 (s, 1H, CH on C-5); 4.85–4.98 (m, 2H, CH on C-6); 5.06 (s, 1H, CH on C-3); 5.20 (s, 1H, CH on C-4). Mass spectrum: 333.0 (M+Na)$^+$.

iii) Conversion of Sulfate 13 into Azide 15

To a solution of the sulfate 13 (2 g, 6.45 mmol) in CH$_3$CN (10 mL) was added Me$_4$N$^+$Cl$^-$ (35 mg) and NaN$_3$ (2.1 g, 32.3 mmol). It was refluxed for 4 h. The reaction was monitored for the disappearance of the starting sulfate by TLC. At the end of the reaction, the solvent was evaporated. To this residue was added dioxane (28 mL) and diluted H$_2$SO$_4$ (conc. H$_2$SO$_4$/H$_2$O 1/5 v/v, 2 mL). The mixture was stirred at RT for 16 h. Solvents were evaporated. The residue was dissolved in EtOAc (80 mL), washed with water (80 mL×2), dried over MgSO$_4$ and solvent evaporated to dryness to obtain 15 (1 g, yield 57/o).

TLC: Silica gel, R$_f$ 0.70, EtOAc/hexane 3/7.

$^1$HNMR (CDCl$_3$, ppm): 1.40, 1.50 (s, 6H, CH$_3$'s on the isopropylidine ring); 3.20 (d, 1H, OH); 3.50 (q, 2H, CH$_2$); 3.75 (s, 3H, OCH$_3$); 4.18 (d, 1H, CH on C4); 4.30 (m, 1H, CH on C-5); 4.65 (s, 1H, CH on C-3). Mass spectrum: 296.1 (M+Na)$^+$.

Example 3B

From the Tosylate 17 (Scheme 3)

i) Methyl (3aS,5R,6S,6aR)-6-hydroxy-2,2-dimethyl-5-({[(4-methylphenyl)sulfonyl]oxy}methyl)dihydrofuro[2,3-d][1,3]dioxole-3a(5H)-carboxylate 17

To a solution of 11 (1.0 g, 4.0 mmol) in pyridine (13 mL, Aldrich) at 0° C. (ice water bath) was added TsCl (0.76 g, 4.0 mmol, Aldrich) in portions. The resulting mixture was stirred at room temperature for 16 h. The solvent was removed in vacuo and the residue was partitioned between EtOAc/H$_2$O. The EtOAc layer was washed with H$_2$O (2×40 mL), brine (1×40 mL) and dried over MgSO$_4$. EtOAc was evaporated and the crude material was purified by silica gel chromatography using EtOAc/Hexane. Product 17 was obtained as a white solid (1.0 g; yield 63%).

TLC: Silica gel, R$_f$ 0.85, EtOAc/hexane 7/3.

$^1$HNMR (CDCl$_3$, ppm): 1.40, 1.50 (s, 6H, CH$_3$'s on the isopropylidine ring); 2.44 (CH$_3$ on phenyl ring); 2.88 (d, 1H, OH); 3.85 (s, 3H, OCH$_3$); 4.19, 4.38 (m, 2H, CH$_2$); 4.27 (d, 1H, CH on C-4); 4.50 (m, 1H, CH on C-5); 4.69 (s, 1H, CH on C-3); 7.35, 7.80 (d, 4H, CH's on phenyl ring). Mass spectrum: 425.2 (M+Na)$^+$; 403.2 (M+R)$^+$.

ii) Conversion of Tosylate 17 into Azide 15

To a solution of 17 (400 mg, 1.0 mmol) in DMF (2 mL) was added NaN$_3$ (97 mg, 1.5 mmol). The reaction mixture was heated at 100° C. (oil bath) for 20 h. The solvent was removed in vacuo and the residue was partitioned between EtOAc/H$_2$O. The EtOAc layer was washed with H$_2$O (2×20 mL), brine (1×20 mL) and dried over MgSO$_4$. EtOAc was evaporated and the crude material was purified by silica gel chromatography using EtOAc/Hexane. Product 15 was obtained as a white solid (140 mg; yield 52%).

TLC: Silica gel, R$_f$ 0.70, EtOAc/hexane 3/7.

$^1$HNMR (CDCl$_3$, ppm): 1.40, 1.50 (s, 6H, CH$_3$'s on the isopropylidine ring); 3.20 (d, 1H, OH); 3.50 (q, 2H, CH$_2$); 3.75 (s, 3H, OCH$_3$); 4.18 (d, 1H, CH on C-4); 4.30 (m, 1H, CH on C-5); 4.65 (s, 1H, CH on C-3). $^{13}$CNMR (CDCl$_3$, ppm): 25.0, 26.0 (CH$_3$'s on the isopropylidine ring); 49.0 (CH$_2$); 53.5 (OCH$_3$); 74.0, 81.3, 88.0 (CH's); 109.5, 114.5 (C on C-1 & C on the isopropylidine ring); 168.2 (CO). Mass spectrum: 296.1 (M+Na)$^+$. Elemental Analysis: Found: C, 44.34; H, 5.42; N, 15.43%. Calculated for C$_{10}$H$_{15}$N$_3$O$_6$: C, 43.96; H, 5.53; N, 15.38, O, 35.13%.

EXAMPLE 4

The synthesis of Methyl (3aR,5S,6R)-5-(aminomethyl)-6-hydroxy-2,2-dimethyldihydrofuro[2,3-d][1,3]dioxole-3a(5H)-carboxylate 16 is detailed.

To a solution of 15 (1.0 g, 3.7 mmol) in MeOH (30 mL) were added aqueous HCl (conc., 0.32 mL) and palladium, 10 wt. % (dry basis) on activated carbon (wet, Degussa type E101 NE/W, 307 mg, Aldrich). It was hydrogenated at 22 psi for 0.5 h. The mixture was filtered through a Celite cake and the solvent evaporated to dryness. Product 16 was obtained as an off white solid (1.0 g; yield 91.0%).

$^1$HNMR (CDCl$_3$, ppm): 1.40, 1.50 (s, 6H, CH$_3$'s on the isopropylidine ring); 3.48–3.55 (m, 2H, CH$_2$); 3.80 (s, 3H, OCH$_3$); 4.48 (m, 1H, CH on C-4); 4.65 (m, 1H, CH on C-5); 4.80 (m, 1H, CH on C-3). $^{13}$CNMR (CDCl$_3$, ppm): 25.5, 27.0 (CH$_3$'s on the isopropylidine ring); 38.0 (CH$_2$); 53.5 (OCH$_3$); 74.0, 77.5, 88.0 (CH's); 109.5, 114.5 (C on C-1 & C on the isopropylidine ring); 167.0 (CO). Mass spectrum: 248.2 (M+Na)$^+$.

EXAMPLE 5

The synthesis of methyl (3aR,5S,6R,6aS)-6-hydroxy-2,2-dimethyl-5-{[(N-{[4,7,10-tris(2-tert-butoxy-2-oxoethyl)-1,4,7,10-tetraazacyclododecan-1-yl]acetyl}glycyl)amino]methyl}dihydrofuro[2,3-d][1,3]dioxole-3a(5H)-carboxylate 19a is detailed.

i) Synthesis of DOTA-G-tri-t-butyl Ester (4)

Preparation of N-(chloroacetyl)-glycine Benzyl Ester (1)

To a suspension of glycine benzylester hydrochloride (25.2 g, 12.5 mmol, Aldrich) in CH$_2$Cl$_2$ (200 ml) was added a solution of K$_2$CO$_3$ (77 g, 55.8 mmol) in H$_2$O (200 ml). The mixture was cooled to 0° C. and chloroacetylchloride (21.0 g, 18.6 mol, Aldrich) was added dropwise in 15 min. The mixture was warmed to room temperature and stirred for 2 h. The two layers were separated and the aqueous layer was extracted with CH$_2$Cl$_2$ (100 ml). The organic layers were combined and washed with H$_2$O (100 ml), brine (100 ml), dried (MgSO$_4$). Evaporation of solvent afforded a light yellowish glassy solid. This was triturated with 250 ml of hexane. The colorless solid was collected and dried to give 30.0 g of the material 1.

Yield: 100% TLC: $R_f$ 0.8 (silica gel, 30% EtOAc/hexane).
$^1$HNMR (CDCl$_3$): δ 4.09 and 4.05 (2s, 6H, NCH$_2$ and COCH$_2$Cl); 5.18 (s, 2H, benzylic CH$_2$); 7.15 (s, 1H, NH); 7.34 (s, 5H, ArH).

Preparation of DOTA-G-tri-t-butyl-benzyl Ester (3)

To a suspension of DO3A tri-t-butyl ester hydrochloride 2 (55.0 g, 100 mmol) in acetonitrile (250 ml) was added anhydrous K$_2$CO$_3$ (50.0 g, 360 mmol). After 15 min. of stirring at room temperature a solution of 1 (29.0 g, 120 mmol) in 50 ml of acetonitrile was added in 15 min. The mixture was stirred at room temperature for 24 h. K$_2$CO$_3$ was filtered off and solvent evaporated. The residue was dissolved in EtOAc (300 ml) and washed with H$_2$O (150 ml), brine (100 ml) and dried MgSO$_4$). The EtOAc solution was concentrated to 150 ml in vacuo and 50 ml of hexane was added. The product crystallized out on keeping the solution at room temperature for 2 h. The crystals were filtered and dried. 51.5 g of the material 3 was obtained as a colorless crystalline solid.

Yield: 73%. TLC: $R_f$ 0.55 (silica gel, 5% MeOH/CHCl$_3$).
$^1$HNMR(CDCl$_3$): δ 1.41(s,27 H, CH$_3$); 1.70–4.42 (26 H, CH$_2$); 5.10 (s, 2H, benzylic CH$_2$); 7.34 (m, 5H, ArH); 9.53 (s, 1H, NH). Mass Spectrum: 720.4 (M+H)$^+$, 742.3 (M+Na)$^+$, 664, 608, 552

Preparation of DOTA-G-tri-t-butyl Ester (4)

To a solution of 3 (10.8 g, 15 mol) in MeOH (50 ml) was added palladium, 10 wt. % (dry basis) on activated carbon (wet, Degussa type E101 NE/W, 2.0 g). The mixture was hydrogenated at 50 psi for 4 h. The catalyst was filtered through a celite cake and evaporation of solvent afforded 8.8 g of 4 as a colorless solid.

Yield: 94%
TLC: $R_f$ 0.2 (silica gel, 5% MeOH/HCl$_3$).
HPLC system: Retention Time 18.63 min; Assay: >100% (area %);
Column: YMC, C18; 0.46×25 cm; solvent: Water(0.1% TFA)-Acetonitrile(0.1% TFA),
Initial condition, 15% ACN, Linear gradient to 55% ACN in 20 min and then to 90% CH$_3$CN in 40 min; Flow rate: 1.0 mL/min; Detection UV λ=220.
$^1$HNMR(CDCl$_3$): δ 4.07(s, 27 H, CH$_3$); 1.80–4.35 (bm, 28 H, CH$_2$), 8.35 (s, 1H, NH). Mass Spectrum: 630.4 (M+H)$^+$, 652.4 (M+Na)$^+$, 574, 518, 462.

ii) Synthesis of methyl (3aR,5S,6R,6aS)-6-hydroxy-2,2-dimethyl-5-{[(N-{[4,7,10-tris(2-tert-butoxy-2-oxoethyl)-1,4,7,10-tetraazacyclododecan-1-yl]acetyl}glycyl)amino]methyl}dihydrofuro[2,3-d][1,3]dioxole-3a(5H)-carboxylate 19a To a solution of 16 (0.9 g, 3.2 mmol) in CH$_2$Cl$_2$ (6 mL) was added 4 (2.0 g, 3.2 mmol), HATU [O-(7-azabenzotriazol-1-yl)-1,1,3,3-tetramethyluronium hexafluorophosphate] (1.2 g, 3.2 mmol, PerSeptive Biosystems), and triethylamine (0.64 g, 6.4 mmol, Aldrich). The clear solution was stirred at room temperature for 4 h. Solvents were evaporated and it was dissolved in EtOAc (50 mL). It was washed with 5% NaHCO$_3$ (2×30 mL), 0.05 N HCl (2×30 mL), H$_2$O (1×30 mL), and dried (MgSO$_4$). Evaporation of solvent afforded product 19a (2.3 g; yield 84%).

TLC: Silica gel, $R_f$ 0.70, MeOH/CHCl$_3$ 1/4.
$^1$HNMR (CDCl$_3$, ppm): 1.38–1.50 (m, 33H, CH$_3$'s on t-Bu's & on isopropylidene ring); 1.90–3.60 (m, 28H, NCH$_2$COOtBu, NCH$_2$CH$_2$, C̲H̲$_2$CONHCH$_2$CONH, CH$_2$CONHC̲H̲$_2$CONH & CONHCH$_2$CONHC̲H̲$_2$); 3.70 (s, 3H, OCH3); 4.02, 4.25, 4.80 (m, 3H, CH's on the gulonic ring); 6.75, 6.95 (t, 2H, NH's). Mass spectrum: 859.6 (M+H)$^+$.

EXAMPLE 6

The synthesis of (3aR,5S,6R,6aS)-6-hydroxy-2,2-dimethyl-5-{[(N-{[4,7,10-tris(2-tert-butoxy-2-oxoethyl)-1,4,7,10-tetraazacyclododecan-1-yl]acetyl}glycyl)amino]methyl}dihydrofuro[2,3-d][1,3]dioxole-3a(5H)-carboxylic acid 20a is detailed.

To a solution of 19a (1.0 g, 1.17 mmol) in MeOH (2 mL) was added a solution of LiOH.H$_2$O (48.5 mg, 1.17 mmol, Aldrich). The resulting solution was stirred at room temperature for 4 h. Solvents were evaporated and the residue was purified by silica column chromatography. Product 20a was obtained as a white solid (0.8 g; yield 81%).

TLC: Silica gel, $R_f$ 0.25, MeOH/CHCl$_3$ 1/9.
$^1$HNMR (CDCl$_3$, ppm): 1.38–1.50 (m, 33H, CH$_3$'s on t-Bu's & on isopropylidene ring); 1.90–3.60 (m, 28H, NCH$_2$COOtBu, NCH$_2$CH$_2$, C̲H̲$_2$CONHCH$_2$CONH, CH$_2$CONHC̲H̲$_2$CONH & CONHCH$_2$CONHC̲H̲$_2$); 4.02, 4.25, 4.80 (m, 3H, CH's on the gulonic ring. Mass spectrum: 845.5 (M+H)$^+$.

EXAMPLE 7

The synthesis of 1,4,7,10-tetraazacyclododecane-1,4,7-triacetic acid, 10-[2-[[2-[[(2R)-2-[(2S)-2,5-dihydro-3,4-dihydroxy-5-oxo-2-furanyl]-2-hydroxyethyl]amino]-2-oxoethyl]amino]2-oxoethyl]-21a is detailed.

20a (1.3 g, 1.58 mmol) was dissolved in 6N HCl/THF (1/1, v/v, 30 mL). The solution was stirred at 45° C. for 6.5 h. The solvents were evaporated to dryness. The residue was dissolved in H$_2$O (30 mL) and purified by preparative BPLC employing a YMC C-18 column. The column was eluted at 15 mL/min., 0% CH$_3$CN/H$_2$O (both containing 0.1% TFA). Fractions were lyophilized to give pure 21a as a white fluffy solid (0.3 g; yield 30.2%).

$^1$HNMR (D$_2$O, ppm): 2.90–4.05 (m, NCH$_2$COOH, NCH$_2$CH$_2$, C̲H̲$_2$CONHCH$_2$CONH, CH$_2$CONHC̲H̲$_2$CONH, CONHCH$_2$CONHC̲H̲$_2$, CHOH & OCH on ascorbic ring). Mass spectrum: 619.3 (M+H)$^+$.

HPLC: Column: YMC C-18. Conditions: 3% CH$_3$CN/H$_2$O (both containing 0.1% TFA), UV at 254 nm; flow rate 1.0 mL/min.; $t_R$: 5.14 min.

Elemental Analysis: Found: C, 36.91; H, 4.56; N, 9.36%. Calculated for C$_{24}$H$_{38}$N$_6$O$_{13}$.2.4TFA.2H$_2$O: C, 37.26; H, 4.83; N, 9.06, O 34.13, F 14.74%.

EXAMPLE 8

The synthesis of 1,4,7,10-tetraazacyclododecane-1,4,7-triacetic acid, 10-[2-[[2-[[(2R)-2-[(2S)-2,5-dihydro-3,4-dihydroxy-5-oxo-2-furanyl]-2-hydroxyethyl]amino]-2-oxoethyl]amino]2-oxoethyl]-, gadolinium salt 22a is detailed.

To a suspension of 21a (86 mg, 0.093 mmol) in H$_2$O (30 mL) was added 1N NaOH (Aldrich) solution to adjust the pH to 5. A solution of Gd(OAc)$_3$ (62.2 mg, 0.15 mmol, Aldrich) in H$_2$O (5 mL) was added and the pH of the mixture was maintained at pH 6 by adding 1N NaOH. The cloudy solution was stirred at room temperature for 16 h, then was warmed to 50° C. for 4 h. The suspension was filtered and purified by preparative HPLC employing a YMC C-18 column. The column was eluted at 15 mL/min., 0% CH$_3$CN/

$H_2O$. Fractions were lyophilized to give pure material 22a as a white fluffy solid (50 mg; yield 63.3%).

Mass spectrum: 774.2 $(M+H)^+$.

HPLC: Column: YMC C-18. Conditions: 3% $CH_3CN/H_2O$ (both containing 0.1% TFA), UV at 254 nm; flow rate 1.0 mL/min.; $t_R$: 7.86 min.

Elemental Analysis: Found: C, 33.81; H, 4.87; N, 9.47, Gd 18.50%. Calculated for $C_{24}H_{35}N_6O_{13}Gd.4.5H_2O$: C, 33.76; H, 5.19; N, 9.84; Gd, 18.42; O, 32.79%.

EXAMPLE 9

The synthesis of methyl (3aS,5S,6S,6aR)-6-hydroxy-2,2-dimethyl-5-({[(4-{[(N-{[4,7,10-tris(2-tert-butoxy-2-oxoethyl)-1,4,7,10-tetraazacyclododecan-1-yl]acetyl}glycyl)amino]methyl}cyclohexyl)carbonyl]amino}methyl)dihydrofuro [2,3-d][1,3]dioxole-3a(5H)-carboxylate 19b is detailed.

i) Synthesis of 6-[trans-4-(aminomethyl)-cyclohexyl-1-carbonyl]-amino-6-deoxy-2,3-isopropylidene-2-keto-gulonate 18

Preparation of 4-{[(phenylmethoxy)carbonylamino]methyl}cyclohexanecarboxylic acid 23

To a solution of trans-4-(aminomethyl)cyclohexanecarboxylic acid (10 g, 63.6 mmol, Aldrich) in 2N aqueous NaOH (65 ml) at 0° C. was added benzyl chloroformate (11.9 g, 70 mmol, Aldrich) and the reaction temperature was maintained below 10° C. The cloudy mixture was stirred at RT for 0.5 h. It was then diluted with $H_2O$ (100 ml). The clear solution was washed with ether (3×80 ml). The pH of the aqueous layer was adjusted to 2 by adding 6N HCl. The precipitates were filtered and dried in vacuo. 17.8 g of 23 was obtained as a white solid.

Yield: 96%. $^1$HNMR ($CDCl_3$, ppm): 0.90–2.30 (m, 9H, $CH_2$'s & CH's on cyclohexyl); 2.20–2.30 (m, 1H, C$\underline{H}$COOH); 2.95–3.05 (m, 2H, $NCH_2$); 4.80–4.85 (m, 1H, NH); 5.10 (s, 2H, PhC$\underline{H}_2$); 7.30–7.40 (m, 5H, CH's on phenyl ring). Mass spectrum: $(M+H)^+$ at 292.2.

Preparation of methyl(1S,5S,7S,6R)-6-hydroxy-3,3-dimethyl-2,4,8-trioxa-7-{[4-{[(phenylmethoxy)carbonylamino]methyl}cyclohexyl)carbonylamino]methyl}bi cyclo[3.3.0]octanecarboxylate 24

To a solution of 16 (2.0 g, 7.1 mmol) in $CH_2Cl_2$ (40 ml) was added 23 (2.1 g, 7.1 mmol), HATU [O-(7-azabenzotriazol-1-yl)-1,1,3,3-tetramethyluronium hexafluorophosphate] (2.7 g, 7.1 mmol, PerSeptive Biosystems). It was cooled to 0° C. by ice-water bath. To this mixture triethylamine (1.43 g, 14.2 mmol Aldrich) was added and the mixture was stirred at 0 C for 4 h. Solvents were evaporated and it was dissolved in EtOAc (100 ml). It was washed with 5% $NaHCO_3$ (2×50 ml), 0.05 N HCl (2×50 ml), $H_2O$ (1×50 ml), and dried ($MgSO_4$). Evaporation of the solvents and silica gel chromatography purification using $MeOH/CHCl_3$ afforded 3 g of 24 as a white solid.

Yield: 81% TLC: Silica gel, $R_f$ 0.50, $MeOH/CHCl_3$ 1/20. $^1$HNMR ($CDCl_3$, ppm): 1.36, 1.46 (s, 6H, $CH_3$'s on isopropylidene ring); 0.85–0.95 (m, 10H, $CH_2$'s and CH's on cyclohexyl); 2.98–3.02 (m, 2H, OCONHC$\underline{H}_2$); 3.80 (s, 3H, $OCH_3$); 3.95–4.15 (m, 2H, CONHC$\underline{H}_2$); 4.52–4.85 (m, 3H, CH's on the gulonic ring); 5.03 (s, 2H, $CH_2Ph$); 7.21–7.35 (m, 5H, CH's on phenyl ring). Mass spectrum: $(M+H)^+$ at 521.3.

Preparation of 6-[trans-4-(aminomethyl)-cyclohexyl-1-carbonyl]-amino-6-deoxy-2,3-isopropylidene-2-keto-gulonate 18

To a solution of 24 (2.9 g, 5.6 mmol) in MeOH (60 mL) was added palladium, 10 wt. % (dry basis) on activated carbon (wet, Degussa type E101 NE/W, 1.0 g, Aldrich). The mixture was hydrogenated at 50 psi for 16 h. Pd/C was filtered through a celite cake and solvent evaporated. 2.0 g of the material 18 was obtained.

Yield: 93%. $^1$HNMR (MeOH, ppm): 1.36, 1.46 (s, 6H, $CH_3$'s on isopropylidene ring); 0.95–2.15 (m, 10H, $CH_2$'s and CH's on cyclohexyl); 2.65 (m, 2H, $NH_2C\underline{H}_2$); 3.20–3.30 (m, 2H, $NCH_2$); 3.60, 4.0, 4.25 (m, 3H, CH's on the gulonic ring); 3.75 (s, 3H, $OCH_3$). Mass spectrum: $(M+H)^+$ at 387.2.

ii) Synthesis of Methyl (3aS,5S,6S,6aR)-6-hydroxy-2,2-dimethyl-5-({[(4-{[(N-{[4,7,10-tris(2-tert-butoxy-2-oxoethyl)-1,4,7,10-tetraazacyclododecan-1-yl]acetyl}glycyl)amino]methyl}cyclohexyl)carbonyl]amino}methyl)dihydrofuro [2,3-d][1,3]dioxole-3a(5H)-carboxylate 19b To a solution of 18 (2.0 g, 5.2 mmol) in $CH_2Cl_2$ (30 mL) was added 6 (3.3 g, 5.2 mmol), HATU (2.0 g, 5.2 mmol, PerSeptive Biosystems). The mixture was cooled to 0° C. by ice-water bath and triethylamine (0.53 g, 5.2 mmol, Aldrich) was added. The clear solution was stirred at 0° C. for 4 h. Solvents were evaporated and the residue was dissolved in EtOAc (100 mL). It was washed with 5% $NaHCO_3$ (2×50 mL), 0.05 N HCl (2×50 mL), $H_2O$ (1×50 mL), and dried $MgSO_4$). Evaporation of solvent and purification by silica gel chromatography using $MeOH/CHCl_3$ afforded product 19b (1.5 g; yield 29%).

TLC: Silica gel, $R_f$ 0.75, $MeOH/CHCl_3$ 1/10.

$^1$HNMR ($CDCl_3$, ppm): 1.0–2.13 (m, 10H, $CH_2$'s & CH's on cyclohexyl ring); 1.43 (m, 27 H, $CH_3$'s on t-Bu's); 1.40, 1.50 (s, 6H, $CH_3$'s on isopropylidene ring); 1.90–3.60 (m, 28H, $NCH_2COOtBu$, $NC\underline{H}_2CH_2$, $NCH_2C\underline{H}_2$, $C\underline{H}_2CONHCH_2CONH$, $CH_2CONHC\underline{H}_2CONH$ & $CH_2$ adjacent to cyclohexyl ring); 3.82 (s, 3H, $OCH_3$); 3.95 (m, 2H, $CH_2$ adjacent to gulonic ring); 4.19, 4.90, 5.12 (m, 3H, CH's on the gulonic ring); 6.32, 6.48, 6.80 (t, 3H, NH's). Mass spectrum: 998.6 $(M+H)^+$.

EXAMPLE 10

The synthesis of (3aS,5S,6S,6aR)-6-hydroxy-2,2-dimethyl-5-({[(4-{[(N-{[4,7,10-tris(2-tert-butoxy-2-oxoethyl)-1,4,7,10-tetraazacyclododecan-1-yl]acetyl}glycyl)amino]methyl}cyclohexyl)carbonyl]amino}methyl)dihydrofuro [2,3-d][1,3]dioxole-3a(5H)-carboxylic acid 20b is detailed.

To a solution of 19b (1.5 g, 1.5 mmol) in MeOH (4 mL) was added a solution of $LiOH.H_2O$ (63 mg, 1.5 mmol, Aldrich). The resulting solution was stirred at room temperature for 4 h. 30 mg of $LiOH.H_2O$ was added and it was stirred at RT for 20 more hours. Solvents were evaporated to obtain crude product 20b (1.45 g; crude yield 99%). The material was used without further purification.

TLC: Silica gel, $R_f$ 0.20, $MeOH/CHCl_3$ 15/100.

$^1$HNMR (MeOH, ppm): 0.85–2.05 (m, 43H, $CH_2$'s & CH's on cyclohexyl ring, $CH_3$'s on t-Bu's & on isopropylidene ring); 1.90–3.60 (m, 28H, $NCH_2COOtBu$, N C$\underline{H}_2CH_2$, $NC\underline{H}_2CH_2$, $C\underline{H}_2CONHCH_2CONH$, $CH_2CONH$ C$\underline{H}_2CONH$ & $CH_2$ adjacent to cyclohexyl ring); 3.48 (m, 2H, $NCH_2$ adjacent to gulonic ring); 3.90, 4.19, 4.40 (m, 3H, CH's on the gulonic ring). Mass spectrum: 984.6 $(M+H)^+$.

EXAMPLE 11

The synthesis of 1,4,7,10-tetraazacyclododecane-1,4,7-triacetic acid, 10-[2-[[2-[[[4-[[[(2R)-2-[(2S)-2,5-dihydro-3,4-dihydroxy-5-oxo-2-furanyl]-2-hydroxyethyl]amino]carbonyl]cyclohexyl]methyl]amino]-2-oxoethyl]amino]2-oxoethyl]-21b is detailed.

20b (1.41 g, 1.43 mmol) was dissolved in 6N HCl/THF (1/1, v/v, 30 mL). The solution was stirred at 45° C. for 6.5 h. The solvents were evaporated to dryness. The residue was dissolved in $H_2O$ (30 mL) and purified by preparative HPLC employing a YMC C-18 column (250×30 mm). The column was eluted at 25 mL/min., 0% $CH_3CN/H_2O$ (both containing 0.1% TFA) for 15 min., then 0%–20% in 60 min. Fractions were lyophilized to give pure 21b as a white fluffy solid (325 mg; yield 30%).

$^1$HNMR ($D_2O$, ppm): 0.78–2.20 (m, 10H, $CH_2$'s & CH's on cyclohexyl ring); 2.90–3.95 (m, 32 H, $NCH_2COOH$, N $CH_2CH_2$, $NCH_2CH_2$, $CH_2CONHCH_2CONH$, $CH_2CONH$ $CH_2CONH$, $CONHCH_2CONHCH_2$, $CONHCH_2CHOH$, $CHOH$ & OCH on ascorbic ring). $^{13}$CNMR ($D_2O$, ppm): 31.9, 32.0. and 32.9 (four Cyclohexyl methylene carbons), 39.5 and 48.0 (two Cyclohexyl methine carbons), 45.5, 46.3, and 48.0 (fifteen $N-CH_2-$ carbons), 70.0 and 79.5 (two ascorbic ring methine carbons), 121.0 and 158.5 (two olefinic carbons), 176.5, 183.5, and 184.6 (seven carbonyl carbons). Mass spectrum: 758.3 $(M+H)^+$.

HPLC: Column: YMC C-18. Conditions: 7% $CH_3CN/H_2O$ (both containing 0.1% TFA), WV at 254 nm; flow rate 1.0 mL/min.; $t_R$: 7.65 min.

Elemental Analysis: Found: C, 42.81; H, 5.77; N, 9.82%. Calculated for $C_{32}H_{51}N_7O_{14} \cdot 2.0TFA \cdot H_2O$: C, 43.06; H, 5.53; N, 9.77%.

EXAMPLE 12

The synthesis of 1,4,7,10-tetraazacyclododecane-1,4,7-triacetic acid, 10-[2-[[2-[[[4-[[[(2R)-2-[(2S)-2,5-dihydro-3,4-dihydroxy-5-oxo-2-furanyl]-2-hydroxyethyl]amino]carbonyl]cyclohexyl]methyl]amino]-2-oxoethyl]amino]2-oxoethyl]-, gadolinium salt 22b is detailed.

To a suspension of 21b (100 mg, 0.132 mmol) in $H_2O$ (20 mL) was added 1N NaOH (Aldrich) solution to adjust the pH to 5. A solution of $Gd(OAc)_3$ (58.99 mg, 0.15 mmol, Aldrich) in $H_2O$ (5 mL) was added and the pH of the mixture was maintained at pH 6 by adding 1N NaOH. The cloudy solution was stirred at room temperature for 16 h. The suspension was filtered and purified by preparative HPLC employing a YMC C-18 column (250×20 mm). The column was eluted at 20 mL/min., 0% $CH_3CN/H_2O$, then 0%–20% in 60 min. Fractions were lyophilized to give pure material 22b as a white fluffy solid (68mg; yield 56.4%).

Mass spectrum: 913.3 $(M+H)^+$.

$^1$HPLC: Column: YMC C-18. Conditions: 7% $CH_3CN/H_2O$ (both containing 0.1% TFA), UV at 254 nm; flow rate 1.0 mL/min.; $t_R$: 10.72 min.

Elemental Analysis: Found: C, 36.81; H, 5.40; N, 9.11; Gd, 15.09%; Calculated for $C_{32}H_{47}N_7O_{14}GdNa \cdot 6.0H_2O$: C, 36.88; H, 5.71; N, 9.41; Gd, 15.09%.

As previously stated, detailed embodiments of the present invention are disclosed herein; however, it is to be understood that the disclosed embodiments are merely exemplary of the invention that may be embodied in various forms. It will be appreciated that many modifications and other variations that will be appreciated by those skilled in the art are within the intended scope of this invention as claimed below without departing from the teachings, spirit and intended scope of the invention.

All publications, patents, and patent applications mentioned in this specification are herein incorporated by reference to the same extent as if each independent publication, patent, or patent application was specifically and individually indicated to be incorporated by reference.

What is claimed is:

1. A compound having the following chemical structure:

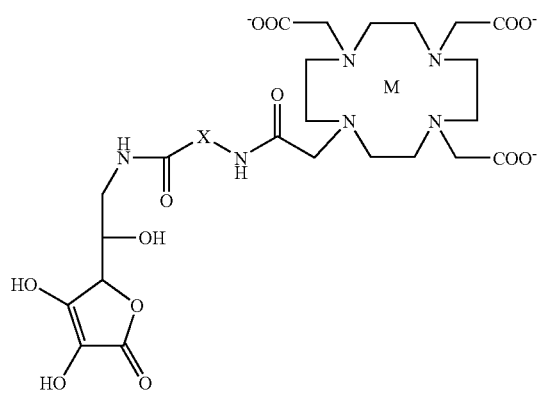

wherein M is $^{99m}Tc$, $^{51}Cr$, $^{67}Ga$, $^{68}Ga$, $^{111}In$, $^{168}Yb$, $^{140}La$, $^{90}Y$, $^{88}Y$, $^{86}Y$, $^{153}SM$, $^{166}HO$, $^{165}Dy$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{215}Bi$, $^{177}Lu$, chromium (III), manganese (II), iron (II), iron (IL), cobalt (II), nickle (II), copper (II), praseodymium (III), neodymium (III), samarium (III), gadolinium (III), terbium, (III), dysprosium (III), holmium (III), erbium (III) or ytterbium (III); and X is $CH_2$,

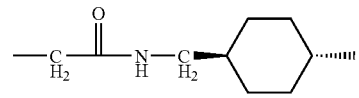

an amino acid, a peptide, or an antibody.

2. The compound of claim 1, wherein X is $CH_2$.

3. The compound of claim 1, wherein X is

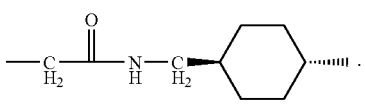

4. The compound of claim 2 or 3, wherein M is $^{99m}Tc$, $^{186}Re$, $^{188}Re$, $^{90}Y$, $^{88}Y$, $^{86}Y$, $^{177}Lu$, or gadolinium (III).

5. A compound having the structure:
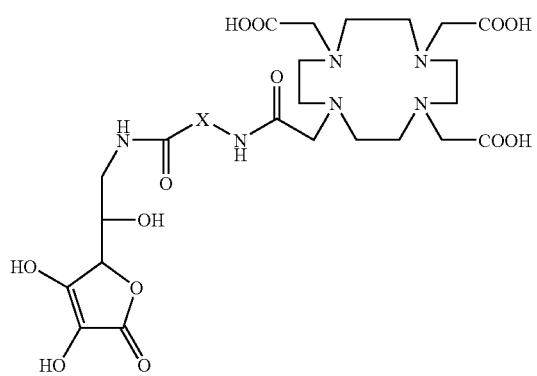
X is CH$_2$,
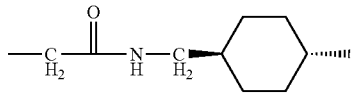
an amino acid, a peptide, or an antibody.
6. The compound of claim 5, wherein X is CH$^2$.
7. The compound of claim 5, wherein X is
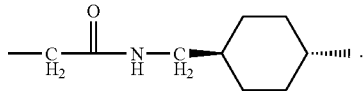
* * * * *